United States Patent
Akita et al.

(10) Patent No.: US 11,413,462 B2
(45) Date of Patent: Aug. 16, 2022

(54) CARDIAC NET HAVING AT LEAST ONE ELECTRODE

(71) Applicant: iCorNet Laboratory Co., Ltd., Nagoya (JP)

(72) Inventors: Toshiaki Akita, Nagoya (JP); Toshiya Sasaki, Nagoya (JP)

(73) Assignee: iCorNet Laboratory Co., Ltd., Aichi (JP)

(*) Notice: Subject to any disclaimer, the term of this patent is extended or adjusted under 35 U.S.C. 154(b) by 0 days.

(21) Appl. No.: 17/076,450

(22) Filed: Oct. 21, 2020

(65) Prior Publication Data
US 2021/0268280 A1    Sep. 2, 2021

Related U.S. Application Data

(63) Continuation of application No. PCT/JP2020/007987, filed on Feb. 27, 2020.

(51) Int. Cl.
*A61N 1/05* (2006.01)
*A61N 1/362* (2006.01)
*A61N 1/375* (2006.01)
*A61N 1/39* (2006.01)

(52) U.S. Cl.
CPC ......... *A61N 1/3621* (2013.01); *A61N 1/0563* (2013.01); *A61N 1/0597* (2013.01); *A61N 1/37512* (2017.08); *A61N 1/39622* (2017.08)

(58) Field of Classification Search
CPC .............. A61N 1/3621; A61N 1/39622; A61N 1/37512; A61N 1/0563; A61N 1/0597
See application file for complete search history.

(56) References Cited

U.S. PATENT DOCUMENTS

| 6,076,013 A | 6/2000 | Brennan et al. |
| 6,169,922 B1 * | 1/2001 | Alferness ............... A61F 2/2481 |
| | | 600/16 |
| 7,640,065 B1 * | 12/2009 | Kroll .................... A61N 1/0597 |
| | | 607/129 |

(Continued)

FOREIGN PATENT DOCUMENTS

| JP | 2009-536560 A | 10/2009 |
| JP | 2011-56182 A | 3/2011 |

(Continued)

*Primary Examiner* — Eric D. Bertram
(74) *Attorney, Agent, or Firm* — Beyer Law Group LLP

(57) ABSTRACT

A cardiac net with at least one electrode enhances the pacing effect on a ventricle. The cardiac net with at least one electrode includes non-conductive portions formed by weaving non-conductive or conductive thread, defibrillation electrodes, and pacing electrodes, which are connected to one another. The defibrillation electrodes are configured to cover the circumference of the heart substantially horizontally, and are placed on an upper side and a lower side of the heart. The pacing electrodes are placed between the defibrillation electrodes and used for sensing the motions of the heart and pacing the ventricle. The pacing electrodes are configured to cover the circumference of the heart substantially horizontally so as to overlay the center of a spiral wave reentry. This configuration allows excitatory stimulus to be applied to the heart from the circumference thereof, thereby enabling the pacing electrodes to perform effective pacing.

10 Claims, 4 Drawing Sheets

(56) References Cited

U.S. PATENT DOCUMENTS

| | | |
|---|---|---|
| 9,566,443 B2 | 2/2017 | de Canniere |
| 10,220,128 B1 * | 3/2019 | Robinson ............ A61M 60/148 |
| 2002/0103511 A1 | 8/2002 | Alferness et al. |
| 2007/0197859 A1 | 8/2007 | Schaer et al. |
| 2015/0018607 A1 * | 1/2015 | Akita .................... D04B 37/02 |
| | | 600/37 |
| 2021/0236833 A1 * | 8/2021 | Akita .................... A61F 2/2481 |

FOREIGN PATENT DOCUMENTS

| | | |
|---|---|---|
| JP | 2016-537178 A | 12/2016 |
| WO | 2007/133947 A2 | 11/2007 |

\* cited by examiner

CARDIAC NET HAVING AT LEAST ONE ELECTRODE

CLAIM OF PRIORITY

This application is a Continuation of International Patent Application No. PCT/JP2020/07987, filed on Feb. 27, 2020, which is hereby incorporated by reference.

BACKGROUND OF THE INVENTION

1. Field of the Invention

The present disclosure relates to a cardiac net that is mounted to the heart for treatment of a heart disease or more specifically a cardiac net equipped with at least one electrode.

2. Description of the Related Art

An implanted cardioverter defibrillator (ICD) may be used to treat tachycardia that is pathological fast pulse, among heart diseases. The implanted cardioverter defibrillator is often used by a method that embeds an electrode at a predetermined position inside of the heart through the blood vessel, electrically connects the embedded electrode with an implanted cardioverter defibrillator body, and applies electric current from the implanted cardioverter defibrillator body to the electrode as needed basis to provide electrical shock therapy for defibrillation. The method of embedding the electrode inside of the heart is highly invasive for the patient and imposes a large burden on the patient. Accordingly, a method of subcutaneously providing an electrode instead of inside of the heart and a method of placing an electrode by using a net or the like that is mounted to outside of the heart have also been proposed.

For example, the prior arts given below describe the techniques of placing the electrode outside of the heart by using a net or the like. United States Patent Application Publication No. 2002/0103511 discloses a technique that weaves conductive wires in a net called jacket to cover over the heart and uses the woven conductive wires as electrodes to receive electric pulses from an implanted cardioverter defibrillator. U.S. Pat. No. 6,076,013 discloses a technique that places electrodes in matrixes of a cardiac cuff to detect the motions of the heart and to be used for ventricular pacing. JP 2009-536560A discloses a technique that places flat plate-like electrodes in a cardiac harness to cover over the heart and a technique that partly removes coating of metal wires forming the harness to be used as electrodes. JP 2016-537178A discloses a technique that provides electrodes in grids of a net mounted to the heart. JP 2011-56182A discloses a technique that separately provides an electrode for defibrillation and an electrode for pacing in an electrode assembly in a flat pad-like shape.

The heart diseases also include a cardiac failure that depresses the motions of the heart due to the phenomenon of cardiomegaly called cardiac remodeling. In the case of such cardiac failure, it has been known that a treatment of wrapping the heart with an elastic cardiac net is effective to suppress the cardiac remodeling.

BRIEF DESCRIPTION OF THE INVENTION

As described above, the electrodes are used for a variety of purposes, for example, defibrillation to remove the ventricular fibrillation occurring in the heart, ventricular pacing to suppress the ventricular tachycardia, and detection of the motions of the heart or sensing. It is, however, said, that biventricular pacing performed to suppress the ventricular tachycardia has only insufficient effects in approximately 30% of cases. Even in these cases, providing the electrodes in a more appropriate configuration is expected to have the better effects. This problem is common to the implanted cardioverter defibrillator and the cardiac resynchronization therapy defibrillator.

In order to solve the problem described above, an object of the present disclosure is to provide a technique of enhancing the effects of pacing in a method of placing electrodes outside of the heart via a net.

According to one aspect of the present disclosure, there is provided a cardiac net with at least one electrode, formed by joining a pacing electrode which is connected with a main device that comprises either an implanted cardioverter defibrillator (ICD) or a cardiac resynchronization therapy defibrillator (CRT/D), with a non-conductive portion and mounted to a heart to wrap outside of the heart. The non-conductive portion is a stretchable mesh made of a non-conductive thread. The pacing electrode is arranged on a lower side of half a height of a cardiac ventricle to be used for pacing and is formed in a strip-like shape to cover half a circumference or more of the cardiac ventricle substantially horizontally.

In any of the conventional methods, i.e., the method of placing the electrode for pacing inside of the heart, the method of subcutaneously placing the electrode for pacing, and the method of placing the electrode for pacing outside of the heart via the net or the like, the electrode for pacing is only either a dot-like electrode or a flat plate-like electrode. The reason why the conventional methods have only insufficient pacing effects may be because it takes time for the excitatory stimulus to reach the heart muscle or the excitatory stimulus unevenly reaches the heart muscle when such a dot-like electrode or a flat plate-like electrode is used. In the configuration of this aspect of the present disclosure, on the other hand, the pacing electrode is provided to cover half the circumference or more of the cardiac ventricle. This configuration enables the excitatory stimulus to be applied synchronously from the substantially entire circumference of the cardiac ventricle and thereby enhances the pacing effect. This configuration is especially effective for pacing to treat a severe case of tachycardia.

In the configuration of this aspect of the present disclosure, the pacing electrode is placed on the lower side of half the height of the cardiac ventricle. This configuration effectively allows the cardiac ventricle to be contracted such as to pump out the blood from the heart.

Furthermore, in this aspect of the present disclosure, forming the non-conductive portion from the stretchable mesh provides another advantage that the electrode is stably placed relative to the heart as a whole. Any of various fibers made of biocompatible materials may be used as the non-conductive thread. For example, the non-conductive thread may be made of polyester, polytetrafluoroethylene or the like. The non-conductive thread may be a single fiber or a strand formed by twisting single fibers. Any of various knitting techniques may be employed to form the non-conductive portion. Some examples include plain knitting and mesh knitting. A knitting technique other than the plain knitting technique may be employed.

In the aspect of the present disclosure, the description of "half the circumference or more of the cardiac ventricle" is defined as a state that a central angle formed by connecting respective ends of the pacing electrode with the center of gravity in a sectional view of the cardiac ventricle cut substantially horizontally is equal to or larger than 180 degrees. The description of "substantially horizontally" does not mean strict horizontality but may include an orientation with a certain degree of inclination. This description indicates a direction in which the pacing electrode is placed in an area that is contracted substantially in synchronism with the motions of the cardiac ventricle to pump out the blood from the heart. The pacing electrode may not be used only for pacing but may have a function of sensing to detect the working conditions of the heart.

According to another aspect of the present disclosure, the pacing electrode may be provided in any of various forms, such as a metal wire rod, a metal plate, or the like. The pacing electrode may be a stretchable mesh made of a conductive thread.

In the above aspect, the stretchability of the mesh also enables the pacing electrode to be stably placed along the heart. Like the non-conductive portion, the mesh may be configured by any of various knitting techniques, such as plain knitting or mesh knitting. Any of various materials may be applicable to the conductive thread. Some examples of the applicable material include tungsten, stainless steel, platinum, platinum iridium alloys, Nitinol and other nickel titanium alloys, carbon nanotubes (CNT), and resin materials filled with conductive fillers. The material to be used may be selected by taking into account the electrical conductivity, the biocompatibility, the knitting ability that indicates the easiness to form the mesh, the strength, the cost and the like. The conductive thread may also be a single fiber or a strand formed by twisting single fibers.

The cardiac net has been known to be effective as a treatment for a cardiac failure that depresses the motions of the heart due to the phenomenon of cardiomegaly called cardiac remodeling. The cardiac net for this purpose preferably has the function of giving an appropriate degree of compression to the heart. An adequate value range for the degree of compression may be determined in advance by simulation. The cardiac net with at least one electrode according to the present disclosure may be configured to have the compressing function in order to suppress the cardiac remodeling by providing the elasticity to give the determined degree of compression.

Because of the reasons given below, however, the cardiac net with at least one electrode according to the present disclosure may be configured to exclude the compressing function against the cardiac remodeling. All the patients who use either the implanted cardioverter defibrillator or the cardiac resynchronization therapy defibrillator are not accompanied with the cardiac remodeling and do not require the compressing function. An applicable procedure for the patients who require the compressing function may further mount an additional cardiac net having the compressing function over the cardiac net with at least one electrode according to the present disclosure. By taking into account the foregoing, the cardiac net with at least one electrode according to the present disclosure may be configured not to have the compressing function and may thus be applicable to both the patients who require and do not require the compressing function without changing the knitting technique according to the requirement or non-requirement of the compressing function. Another advantage is to avoid the difficulty in weaving the cardiac net such as to give a desired degree of compression by using two different materials of the non-conductive thread and the conductive thread.

According to another aspect of the present disclosure, the pacing electrode may be arranged to cover an entire circumference of the cardiac ventricle. This configuration enables the excitatory stimulus to be applied from the entire circumference of the cardiac ventricle and further enhances the pacing effect.

According to another aspect of the present disclosure, the pacing electrode may comprise a first pacing electrode and a second pacing electrode that are connected in parallel with the main device and that are respectively located on an upper side and on a lower side.

The above aspect is a configuration provided with two pacing electrodes. The first and the second pacing electrodes are respectively provided as single strip-like electrodes for a monopolar electrode type of the main device that comprises either the implanted cardioverter defibrillator or the cardiac resynchronization therapy defibrillator. The first and the second pacing electrodes are respectively configured as two strip-like electrodes that respectively serve as a positive electrode and a negative electrode, on the other hand, for a bipolar electrode type of the main device.

The vertical arrangement of the two pacing electrodes on the upper side and on the lower side as described above allows for a variety of applications, so as to further enhance the pacing effect. A first application causes the electric current to be applied from the electrode on the lower side of the heart and from the electrode on the upper side of the heart with a time difference, so as to apply an excitatory stimulus in synchronism with systolic motions of the heart that pump out the blood. A second application applies the electric current to the first electrode and the second electrode simultaneously, so as to synchronize refractory periods of the heart muscle between the two electrodes for a relatively wide range. This may serve as a block line to interrupt an abnormal transmission of an excitatory signal, such as a spiral wave reentry that triggers the ventricular fibrillation. These functions enable the configuration of the above aspect to further enhance the pacing effect. Especially, the configuration of the above aspect is highly effective for pacing to treat tachycardia.

The description of the above aspect does not intend to limit the present disclosure to the configuration provided with the two pacing electrodes. The cardiac net with at least one electrode of the present disclosure may be provided with only one pacing electrode or may be provided with three or more pacing electrodes.

According to another aspect of the present disclosure, the pacing electrode may be arranged to overlay a center of a spiral wave reentry that triggers ventricular fibrillation. A normal signal of transmitting excitation in the heart is transmitted unidirectionally from the cardiac auricle to the cardiac ventricle, whereas an abnormal signal is likely to form a circuit where the signal is turned around in the cardiac ventricle, i.e., a spiral wave reentry. This spiral wave reentry is known as one cause of triggering ventricular tachycardia. By taking into account this cause, the arrangement of the pacing electrode to overlay the center of the spiral wave reentry is expected to effectively suppress the ventricular tachycardia.

The position of the spiral wave reentry may be specified for each patient in advance by simulation, a test or the like. The position of the spiral wave reentry is not strictly fixed to one location but is, in most cases, kept in a certain range even if the position varies. The pacing electrode does not fully lose its effect when the location of the pacing electrode is only slightly different from the center of the spiral wave reentry. Accordingly, the placement of the pacing electrode to overlay the center of the spiral wave reentry specified by the simulation or the like is expected to have the sufficient effect of suppressing the ventricular tachycardia even when the position of the spiral wave reentry slightly varies.

According to another aspect of the present disclosure, the cardiac net with at least one electrode may further comprise a defibrillation electrode that is configured by a stretchable mesh made of a conductive thread and that is connected with the main device to be used for defibrillation of the heart.

In the configuration of the above aspect, the electrode for defibrillation can be placed in a wide range outside of the heart. This configuration effectively performs defibrillation with the smaller electric power, compared with the method of embedding the electrode inside of the heart. The defibrillation electrode is also configured by a mesh of a conductive thread. This configuration provides another advantage that the defibrillation electrode can be placed at an appropriate position of the heart relatively stably along the heart.

The configuration of the above aspect also has other advantages described below. The electric power of electrical shock therapy used for defibrillation of the heart is generally larger than the electric power used for ventricular pacing. Accordingly, the configuration of separately providing the defibrillation electrode using a relatively large electric power for defibrillation and the pacing electrode using a relatively small electric power and electric current for ventricular pacing advantageously facilitates formation of the respective electrodes suitable for their purposes.

Furthermore, for the effective defibrillation, it is important to detect the occurrence or no occurrence of ventricular fibrillation with high accuracy. In the above aspect, the pacing electrode may be configured to have an additional function of sensing. This configuration advantageously allows for highly accurate detection of the ventricular fibrillation without requiring any additional electrode exclusive for sensing.

In the aspect of the cardiac net provided with the pacing electrode and the defibrillation electrode, the defibrillation electrode may comprise defibrillation electrodes respectively placed on an upper side and on a lower side of the heart, and the pacing electrode may be placed between the defibrillation electrodes placed on the upper side and on the lower side.

The effect of defibrillation was examined in different arrangements of the electrode for defibrillation that is placed to cover over the entire circumference of the heart, to be located on an upper side and on a lower side of the heart, to be located on a left side and on a right side of the heart, and to be located on a front side and on a rear side of the heart. It was then found that the vertical arrangement on the upper side and on the lower side had the effect with the smallest electric power. According to this result, it is preferable to place the defibrillation electrodes on the upper side and on the lower side. The configuration of placing the pacing electrode between the defibrillation electrodes enhances the flexibility of the arrangement and enables the pacing electrode to be placed at a position suitable for ventricular pacing.

Like the pacing electrode, the defibrillation electrode may be placed to cover half the circumference or more of the heart substantially horizontally. The defibrillation electrode may also be formed as a pad-like electrode.

In the aspect of the cardiac net provided with the pacing electrode and the defibrillation electrode, the defibrillation electrode may have an area larger than an area of the pacing electrode.

The electric power used for electrical shock therapy for defibrillation is generally larger than the electric power used for ventricular pacing. Setting the areas of the defibrillation electrode and the pacing electrode according to this aspect thus enables the respective electric powers to be used without waste. The sizes of the defibrillation electrode and the pacing electrode may be set arbitrarily, based on the electric powers and the like.

In any of the various aspects described above, the non-conductive portion may be made of an absorbable thread. This configuration reduces a potential risk that the non-conductive portion causes an infection or the like in the body.

In the case where the cardiac net with at least one electrode of the present disclosure is configured not to give the compression to the heart for suppressing the cardiac remodeling, the non-conductive portion only serves to keep the electrode. After the cardiac net with at least one electrode is mounted to the heart, however, the electrode in some shape may not need to be kept by the non-conductive portion. The configuration of the above aspect is especially effective for the non-conductive portion without the function of giving the compression to the heart.

In the case where the non-conductive portion is made of the absorbable thread, the electrode needs to be kept at an appropriate position even after the non-conductive portion is absorbed. From this point of view, it is preferable that the electrode is configured in a shape that goes around the heart. This configuration enables the electrode to be kept at an appropriate position on the heart by the elastic force of the electrode.

According to another aspect of the present disclosure, the cardiac net with at least one electrode may further comprise a connector. The connector may be provided with a jack, which is mounted to the connector to receive insertion of a lead that is standardized to connect with the main device. The jack may be connected with a conductive wire from each electrode of the cardiac net.

This configuration enables the cardiac net with at least one electrode and the main device to be relatively easily connected with each other and suppresses an unexpected breaking of a connection. In general, various standardized leads are present between the electrodes on the heart and the main device that comprises either the implanted cardioverter defibrillator or the cardiac resynchronization therapy defibrillator. Accordingly, it is preferable to use these leads to connect the cardiac net having at least one electrode with the main device in terms of the convenience and the reliability.

The cardiac net having at least one electrode may be connected with the standardized lead by a variety of methods. For example, one available method may detach a plug at a leading end of a lead to make conductive wires in the lead exposed and connect these conductive wires with the respective electrodes of the cardiac net. In the event of breaking of a connection with any of the electrodes, however, this method requires replacement of the entire implanted cardioverter defibrillation device including the cardiac net and the main device. Exposure of the conductive wires at the leading end of the standardized lead is likely to reduce the reliability of the lead.

The configuration of the above aspect, on the other hand, uses the connector and enables the cardiac net having at least one electrode to be connected with the main device by using the standardized lead with no change. Furthermore, in the configuration of this aspect, the cardiac net having at least one electrode and the main device may be individually mounted or placed in the body and may subsequently be connected with each other by means of a lead. This improves the workability of mounting. Placing the main device and the cardiac net having at least one electrode such as to stabilize the position of the connector relative to the cardiac net having at least one electrode suppresses an external force from being applied to the conductive wire connected with the electrode of the cardiac net and thereby suppresses breaking of the connection. Moreover, another advantage is that in the case of a failure of the main device, the requirement is replacement of only the main device without demounting the cardiac net with at least one electrode.

The conductive wire may be connected with the electrode by any of various methods. For example, part of the conductive thread forming the electrode may be extended to outside and used as the conductive wire.

In another example, the conductive wire may be interwoven in a mesh forming each electrode. This method enables the conductive wire to be connected by the relatively simple configuration. Another advantage of this method is the easier manufacture, compared with the method of extending part of the conductive thread forming the electrode. The conductive wire may be interwoven by any of various methods. In one example, the conductive wire may form loops and may be woven into the mesh that forms each electrode.

This configuration provides the conductive wire itself with the stretchability and further effectively suppresses breaking of the connection. This configuration also increases the contact area between the conductive wire and the electrode to ensure the electrical conductivity.

Furthermore, a variety of modes may be adopted for mounting the conductive wire. For example, a plurality of conductive wires may be mounted to each electrode. Even in the event of disconnection of part of the conductive wires, this configuration enables the cardiac net with having at least one electrode to be connected with the main device by using the other conductive wire without requiring replacement of the cardiac net having at least one electrode.

The present disclosure may not necessarily have all the diversity of features described above but may be configured appropriately with partial omission or in combination. The present invention may be implemented by various aspects other than the aspects of the cardiac net having at least one electrode.

For example, according to another aspect of the present disclosure, there is provided an implanted cardioverter defibrillation device, comprising: the cardiac net according having at least one electrode to any of the aspects described above; and a main device that comprises either an implanted cardioverter defibrillator or a cardiac resynchronization therapy defibrillator. The cardiac net having at least one electrode and the main device are connected with each other by means of a conductive wire.

According to another aspect of the present disclosure, there is provided a design method of designing a cardiac net having at least one electrode using a computer. The design method of designing the cardiac net having at least one electrode comprises a step of causing a computer to specify a position of a patient's spiral wave reentry by simulation; and a step of causing the computer to determine a placement position of an electrode such as to overlay a center of the specified position.

DETAILED DESCRIPTION OF EMBODIMENTS OF THE INVENTION

Figure 1:
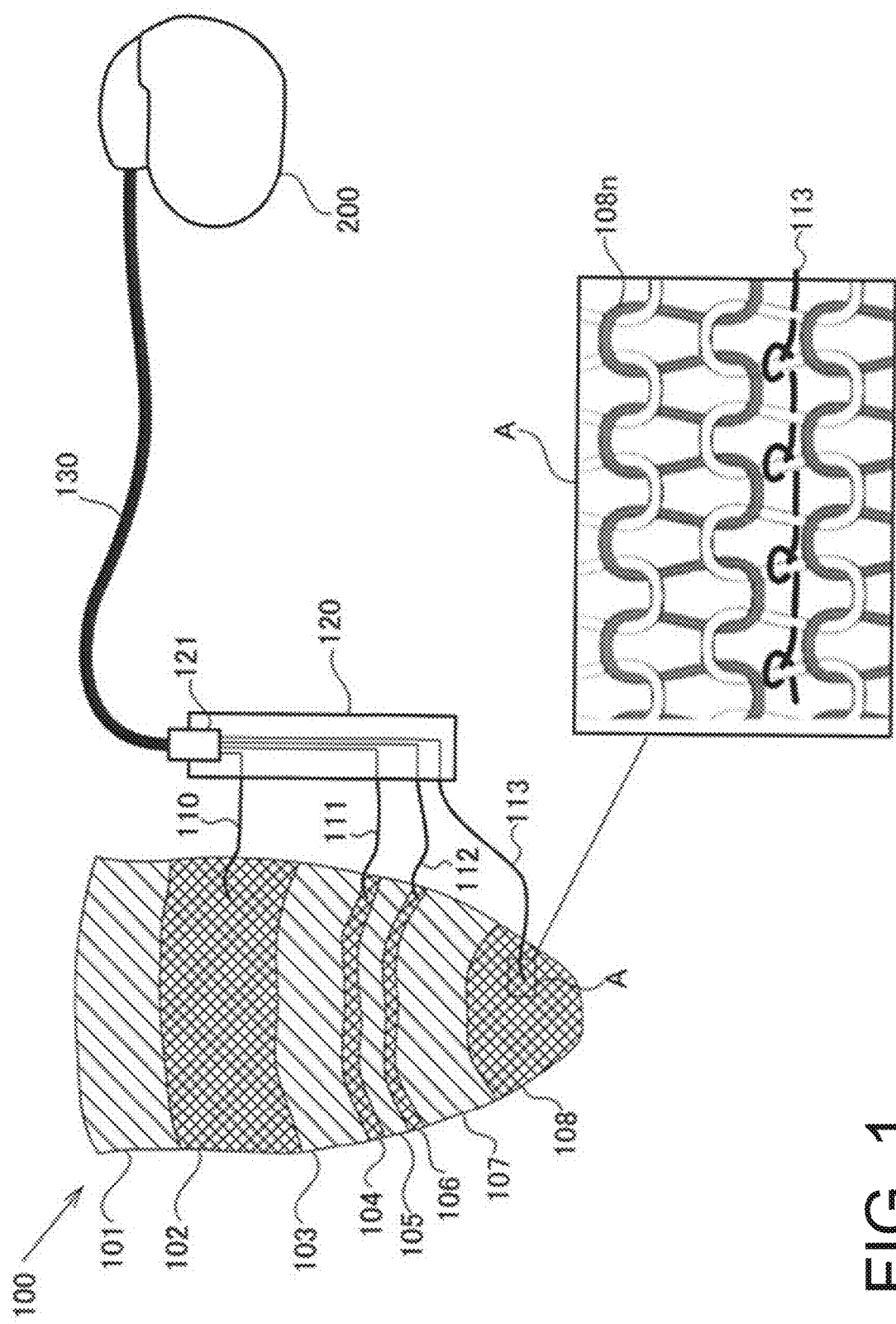
FIG. 1 is an explanatory diagram illustrating the general configuration of an implanted cardioverter defibrillation device.

FIG. 1 is an explanatory diagram illustrating the general configuration of an implanted cardioverter defibrillation device. The implanted cardioverter defibrillation device according to the embodiment is configured by connecting an implanted cardioverter defibrillator body 200 with a cardiac net 100 having at least one electrode by means of a lead 130.

The implanted cardioverter defibrillator body 200 used herein may be one of various existing devices and may be either an implanted cardioverter defibrillator (ICD) or a cardiac resynchronization therapy defibrillator (CRT/D). According to the embodiment, a defibrillator having the functions of detecting the motions of the heart, i.e., sensing, ventricular pacing, and defibrillation is employed for the implanted cardioverter defibrillator body 200. Either a monopolar defibrillator or a bipolar defibrillator may be adopted. The lead 130 used is standardized for connection with the implanted cardioverter defibrillator body 200. The standard may be, for example, DF1, DF4 or IF1.

The cardiac net 100 having at least one electrode is a net mounted to the heart such as to cover up the heart from a lower side thereof. The cardiac net 100 having at least one electrode is formed by connecting non-conductive portions 101, 103, 105 and 107, defibrillation electrodes 102 and 108 and pacing electrodes 104 and 106. The non-conductive portions 101, 103, 105 and 107 are stretchable meshes formed by weaving a non-conductive thread by a plain knitting technique or another technique. The non-conductive thread used may be made of, for example, polyester or polytetrafluoroethylene. The non-conductive thread used may be absorbable thread. According to the embodiment, the pacing electrodes 104 and 106 are also used for sensing that detects the operating conditions of the heart.

The defibrillation electrodes 102 and 108 and the pacing electrodes 104 and 106 are stretchable meshes respectively formed by weaving conductive threads by a plain knitting technique or another technique. Any of various materials may be applicable to the conductive thread. Some examples of the applicable material include tungsten, stainless steel, platinum, platinum iridium alloys, Nitinol and other nickel titanium alloys, carbon nanotubes (CNT), and resin materials filled with conductive fillers. The thickness of the thin thread may be determined arbitrarily and may be, for example, about 20 to 30 micrometers.

According to the embodiment, different materials are used for the defibrillation electrodes 102 and 108 and for the pacing electrodes 104 and 106. Fibers formed from the CNT alone are used for the pacing electrodes 104 and 106. Platinum fine wires are used, on the other hand, for the defibrillation electrodes. In general, defibrillation applies large current for a relatively short time period, whereas pacing applies small current continuously. Accordingly, the defibrillation electrodes have an impedance of about 0.5 to 2 ohms, whereas the pacing electrodes have an impedance of about 150 ohms. This configuration reduces the electric current flowing through the pacing electrodes and thereby extends the life of the battery. Using different materials for the defibrillation electrodes and for the pacing electrodes enables the electrodes to be configured according to the difference in power consumption.

Mutual connection of the non-conductive portions 101, 103, 105 and 107, the defibrillation electrodes 102 and 108 and the pacing electrodes 104 and 106 may be achieved by changing over the non-conductive thread and the conductive thread to be suitable for the respective portions in the process of weaving the cardiac net 100 having at least one electrode from its lower end or more specifically from the defibrillation electrode 108-side or from its upper end or more specifically from the non-conductive portion 101-side. Another procedure may individually weave the respective portions and subsequently connect the respective woven portions with one another.

The defibrillation electrodes 102 and 108 are electrodes used for defibrillation. The pacing electrodes 104 and 106 are electrodes used for sensing the motions of the heart and for ventricular pacing. According to the embodiment, the defibrillation electrodes 102 and 108 are formed to respectively cover the circumference of the heart substantially horizontally and are placed on an upper side and a lower side. The pacing electrodes 104 and 106 are also formed in strip-like shapes such as to cover the circumference of the heart substantially horizontally and are placed between the defibrillation electrodes 102 and 108.

According to the embodiment, the widths of the defibrillation electrodes 102 and 108 are wider than the widths of the pacing electrodes 104 and 106. As a result, the areas of the electrodes 102 and 108 are larger than the areas of the pacing electrodes 104 and 106. In general, the electric power required for defibrillation of the heart is larger than the electric power required for ventricular pacing. The defibrillation electrodes 102 and 108 are the electrodes used for defibrillation of the heart, and the pacing electrodes 104 and 106 are the electrodes used for ventricular pacing. Accordingly, the defibrillation electrodes 102 and 108 and the pacing electrodes 104 and 106 are respectively formed to have the areas according to the electric powers to be supplied. This configuration enables the electric powers to be effectively used according to the respective functions of the electrodes.

The shapes and the placements shown in FIG. 1 are only illustrative. The shapes, the areas, and the locations of the defibrillation electrodes 102 and 108 and the pacing electrodes 104 and 106 may be determined arbitrarily by taking into account the respective functions. For example, the defibrillation electrode may not be necessarily provided to cover around the heart but may be provided as a pad-like electrode.

The defibrillation electrodes 102 and 108 and the pacing electrodes 104 and 106 are connected with a connector 120 by means of conductor wires 110, 111, 112 and 113. The conductor wires 110 to 113 are mounted such as to be woven in the respective electrodes. A closeup view of a connection area A of the defibrillation electrode 108 and the conductor wire 113 is shown on a lower right side in the drawing. As illustrated, a conductive thread 108h is interwoven in the defibrillation electrode 108. The illustrated example is plain stitches.

The conductor wire 113 is mounted such as to be woven in these stitches. In the illustrated example, the conductor wire 113 appropriately forms loops to be woven into the stitches. This configuration enables the conductor wire 113 to be extended and contracted accompanied with extension and contraction of the cardiac net 100 having at least one electrode and thereby suppresses breaking of connection. This configuration also increases the contact area of the conductor wire 113 with the electrode and ensures the electrical conductivity. Any of various other weaving methods, for example, a linearly weaving method or a zigzag weaving method, may be applied for the conductor wire 113. In the case where twisted thread is used for the conductive wire 113, an available procedure may untwist an end of the twisted thread and individually weave respective single yarns of the twisted thread. The conductive wires 110 to 112 are also similarly woven in the respective electrodes.

A jack 121 that fits a plug provided on an end of the lead 130 is mounted to the connector 120. The conductor wires 110 to 113 are electrically connected with the jack 121, such as to enable the functions of defibrillation, sensing and ventricular pacing. This configuration enables the cardiac net 100 having at least one electrode and the implanted cardioverter defibrillator body 200 to be electrically connected with each other by means of the lead 130.

A procedure of mounting the implanted cardioverter defibrillation device inside the human body individually mounts the implanted cardioverter defibrillator body 200 and the cardiac net 100 having at least one electrode and subsequently connects the lead 130 with the connector 120. Using the connector 120 in this manner improves the workability in the process of mounting the implanted cardioverter defibrillation device. Additionally, using the connector 120 suppresses an external force from being applied to the conductor wires 110 to 113 and suppresses unexpected falls of the conductor wires 110 to 113.

Figure 2:
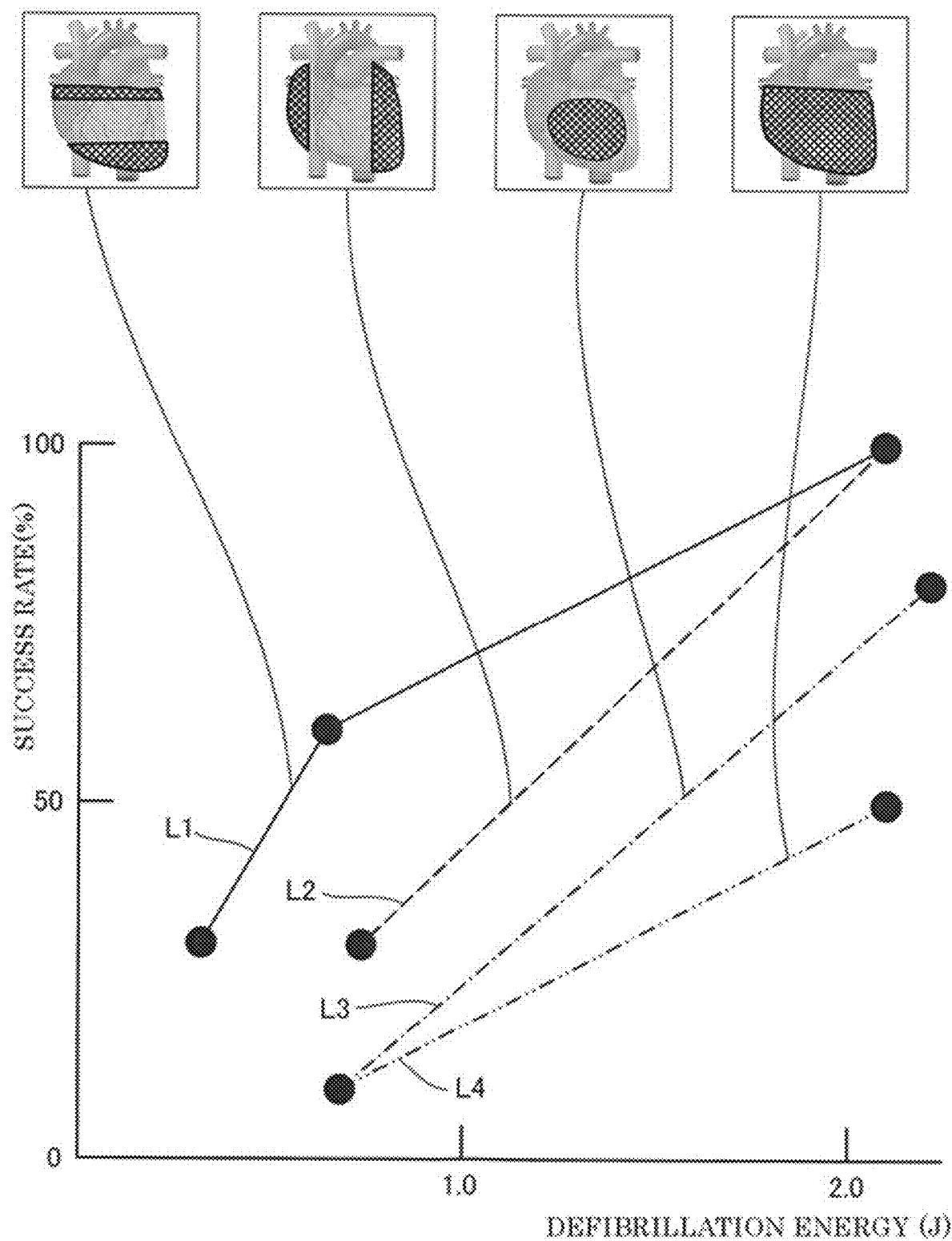
FIG. 2 is a graph illustrating success rates of defibrillation at different placement locations of defibrillation electrodes.

FIG. 2 is a graph illustrating success rates of defibrillation at different placement locations of defibrillation electrodes. The defibrillation electrodes are electrodes used for defibrillation and may be placed at various locations other than the locations shown in FIG. 1. The effects of the electrodes on defibrillation were examined by using the electrodes placed at various locations. An upper half of FIG. 2 schematically illustrates the placement locations of the electrodes corresponding to respective cases. In FIG. 2, a graph L1 shows the result of a case where electrodes are placed on an upper side and a lower side of the heart; a graph L2 shows the result of a case where electrodes are placed on a left side and a right side of the heart; a graph L3 shows the result of a case where electrodes are placed on a front side and a rear side of the heart; and a graph L4 shows the result of a case where electrodes are placed to include and cover the entire heart. As illustrated, the case where the electrodes are placed on the upper side and the lower side of the heart (graph L1) has the highest success rate of defibrillation with regard to a fixed defibrillation energy, compared with all the other cases. It is accordingly expected that placing the electrodes on the upper side and the lower side of the heart is favorable for defibrillation. Based on these results, the defibrillation electrodes 102 and 108 according to the embodiment shown in FIG. 1 are placed on the upper side and the lower side of the heart. These results of the experiment, however, do not exclude the locations other than the upper side-lower side location with regard to the placement of the defibrillation electrodes.

The following describes the placement of the electrodes shown in FIG. 1 more in detail. FIG. 1 is an explanatory diagram illustrating an example of placement locations of electrodes. In this example, the pacing electrode 106 is formed to have such a shape, an area and a placement as to overlay the center of a spiral wave reentry formed in a cardiac ventricle. A curve S in the drawing indicates a spiral wave reentry, and a point C indicates a center of the spiral wave reentry. The spiral wave reentry means such a state that an excitatory signal, which is to be transmitted unidirectionally from the cardiac auricle to the cardiac ventricle, is turned around in a circuit as illustrated, due to some abnormality. It is said that the spiral wave reentry may trigger ventricular tachycardia. In the illustrated embodiment, the pacing electrode 106 is placed to overlay the point C that is the center of this spiral wave reentry. This configuration directly applies an electrical stimulus to the spiral wave reentry that triggers the ventricular tachycardia and thereby enhances the effect of suppressing the ventricular tachycardia.

The position of the spiral wave reentry may be specified by simulation, a test or the like. The position of the spiral wave reentry may, however, not be strictly fixed to one location, and the specification of the position may include some error. It is thus preferable to determine the shape and the area of the pacing electrode 106 such as to cover a potential error and a potential fluctuation of the point C.

According to the embodiment, the pacing electrode 106 is a strip-like electrode provided to cover the circumference of cardiac ventricles substantially horizontally and is placed on a lower side of half a height H of the cardiac ventricles (H/2). This configuration enables an excitatory stimulus to be effectively applied corresponding to the motions of the heart that pump out the blood. The pacing electrode 106 may be a single strip for a monopolar type of the implanted cardioverter defibrillator body 200 and may be two strips that respectively serve as a positive electrode and as a negative electrode and that are arrayed vertically, for a bipolar type of the implanted cardioverter defibrillator body 200.

According to this embodiment, the pacing electrode 104 is provided on an upper side of the pacing electrode 106. Like the pacing electrode 106, the pacing electrode 104 is also a strip-like electrode provided to cover the circumference of the cardiac ventricles substantially horizontally. The pacing electrode 104 may be a single strip for a monopolar type of the implanted cardioverter defibrillator body 200 and may be two strips that respectively serve as a positive electrode and as a negative electrode and that are arrayed vertically, for a bipolar type of the implanted cardioverter defibrillator body 200. The position of the pacing electrode 104 may be set arbitrarily. It is not necessary that the pacing electrode 104 is placed on the lower side of half the height of the cardiac ventricles (H/2).

The widths of the pacing electrodes 104 and 106 in the height direction may be set arbitrarily but are preferably not greater than about 10 millimeters, more preferably not greater than 5 millimeters and furthermore preferably approximately 2 millimeters. The widths of the pacing electrodes 104 and 106 in the height direction are set to approximately 2 millimeters according to the embodiment. The pacing electrodes 104 and 106 are preferably set to provide an impedance of approximately 150 ohms, with a view to reducing the power consumption.

The vertical arrangement of the pacing electrodes 104 and 106 on the upper side and on the lower side allows for a variety of applications. A first application causes the electric current to be applied from the electrode on the lower side of the heart and from the electrode on the upper side of the heart with a time difference, so as to apply an excitatory stimulus in synchronism with systolic motions of the heart that pump out the blood. A second application applies the electric current to the first electrode and the second electrode simultaneously, so as to synchronize refractory periods of the heart muscle between the two electrodes for a relatively wide range. This may serve as a block line to interrupt an abnormal transmission of an excitatory signal, such as a spiral wave reentry that triggers the ventricular fibrillation. These functions enable the configuration of the above embodiment to further enhance the pacing effect. Especially, the configuration of the above embodiment is highly effective for pacing to treat tachycardia. According to a modification, the cardiac net may be provided with only one pacing electrode 106 or may be provided with three or more pacing electrodes.

A horizontal sectional view of the heart is illustrated in a lower half of the drawing. The horizontal sectional view schematically illustrates a right cardiac ventricle RV, a left cardiac ventricle LV and walls of the heart in the periphery of these cardiac ventricles RV and LV. As illustrated, the pacing electrode 106 is placed to cover the entire circumference of the heart. When electric current is applied to the pacing electrode 106, excitatory stimulus is applied from the circumference to the heart synchronously as shown by arrows in the drawing. This configuration accordingly enables the heart to be effectively contracted to pump out the blood. The arrangement of the pacing electrode 106 to cover both the ventricles enables the motions of the two ventricles to be synchronized with each other.

It is, however, not necessary that the pacing electrode 106 covers the entire circumference of the heart. A pacing electrode 106A illustrated in the drawing may be provided in place of the pacing electrode 106. The pacing electrode 106A is provided to cover a left cardiac ventricle LV-side but not to cover a right cardiac ventricle RV-side. A central angle ANG defined by connecting respective ends of the pacing electrode 106A with a center of gravity CG of the heart in this sectional view is larger than 180 degrees. The configuration that the pacing electrode 106 covers half the circumference or more of the cardiac ventricles in such a manner is expected to have the sufficient effect by application of the excitatory stimulus from the circumference of the heart.

In the illustrated example, the pacing electrode 106A is arranged to cover the left cardiac ventricle LV-side. According to modifications, the pacing electrode may be arranged to cover the opposite side, i.e., the right cardiac ventricle RV-side or to cover parts of the respective cardiac ventricles. The pacing electrode may be placed in a variety of arrangements.

According to one modification, one of the pacing electrodes 106 and 104 may be arranged to cover the entire circumference of the cardiac ventricles, while the other pacing electrode may be arranged to cover part of the circumference of the cardiac ventricles.

The pacing electrodes may be set at any positions by taking into account a positional relationship to the defibrillation electrodes. The defibrillation electrodes may, on the other hand, not be necessarily arranged in the vertical direction in the shapes that cover the entire circumference of the heart as shown in FIG. 1 but may employ another arrangement by taking into account the positions of the pacing electrodes.

In response to detection of ventricular tachycardia, a general utilization procedure of the implanted cardioverter defibrillator first applies electric current to the pacing electrode to try ventricular pacing and, in the case of a failure in stopping ventricular fibrillation, uses the defibrillation electrode to perform defibrillation. In this sense, defibrillation is an operation that should be called a last defense to stop an abnormality of the heart and is thus thought to be of the higher importance than ventricular pacing. It is accordingly preferable to determine the shapes, the areas and the positions of the pacing electrode and the defibrillation electrode by giving priority to the defibrillation electrode over the pacing electrode.

Figure 4:
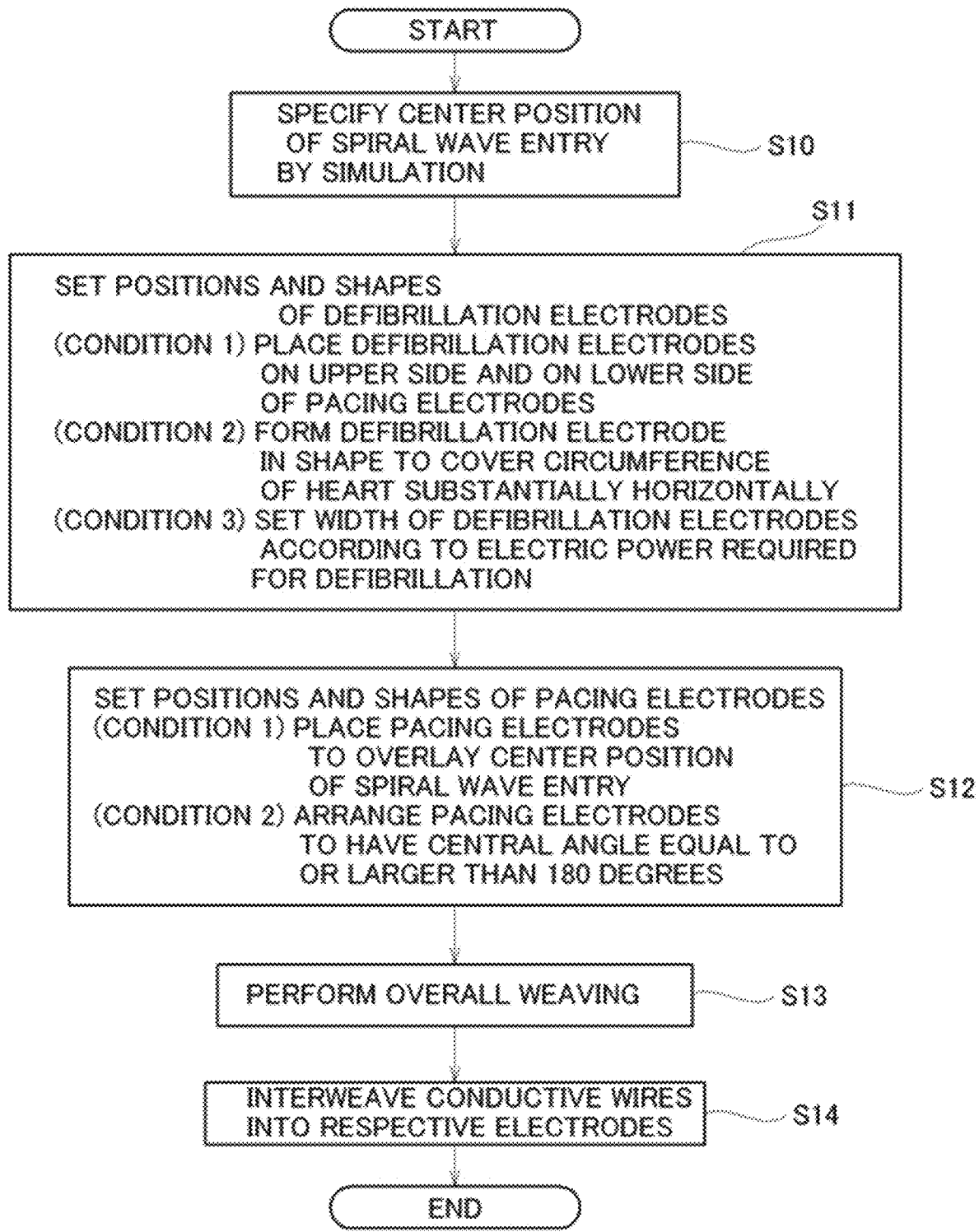
FIG. 4 is a flowchart showing a manufacturing process of a cardiac net having at least one electrode.

FIG. 4 is a flowchart showing a manufacturing process of the cardiac net having at least one electrode. This flowchart shows a procedure of manufacturing the cardiac net having at least one electrode and does not mean that all steps are automatically performed by a computer. This procedure, on the other hand, does not at all exclude the case of using the computer as much as possible. The body that performs this manufacturing process may be a computer or may be a designer (human being). In the description below, a term "performer" is used as a subject including both the computer and the human being.

In this manufacturing process, the performer first specifies a point C that indicates a center position of spiral wave reentry by simulation, test or the like (step S10). Various known methods may be employed for the simulation. In the case of manufacturing a dedicated cardiac net having at least one electrode exclusive for a specific patient, this simulation may be performed by using data of the specific patient as the target. In the case of manufacturing a versatile cardiac net having at least one electrode applicable to a plurality of patients, this simulation may be performed by using data of the plurality of patients. The center position that statistically has a high probability of the occurrence of a spiral wave reentry is then specified, based on the simulation.

After specifying the position of the spiral wave reentry, the performer subsequently sets the positions and the shapes of the electrodes for defibrillation or more specifically the defibrillation electrodes 102 and 108 (step S11). Conditions required for setting are shown in the flowchart. A condition 1 is to place the defibrillation electrodes on the upper side and on the lower side of the electrodes for pacing or more specifically the pacing electrodes 104 and 106. The positions and the like of the electrodes for pacing are set at a subsequent step. The manufacturing process accordingly places the defibrillation electrodes to be arrayed in the vertical direction with providing spaces where the electrodes for pacing are placed. It is preferable to determine the positions and the shapes of the defibrillation electrodes such as not to overlap the center of the spiral wave reentry.

A condition 2 is to form the defibrillation electrodes 102 and 108 in such a shape that covers around the heart substantially horizontally as illustrated. This configuration enables an electrical shock to be applied from the circumference of the heart to the heart and thereby effectively performs defibrillation. Furthermore, forming the defibrillation electrodes in the shape to cover around the heart suppresses a positional shift due to the motions of the heart or the like. In the case where the non-conductive portions are made of an absorbable thread, forming the defibrillation electrode in such a shape to cover around the heart is especially effective to stabilize the position of the electrode.

A condition 3 is to set the width of the defibrillation electrodes according to the electric power required for defibrillation. According to the embodiment, the electrode is formed by using an extremely thin conductive thread, so that the resistance tends to increase with a decrease in the width of the electrode. The electric power for defibrillation supplied in the case of using the cardiac net having at least one electrode of the embodiment is significantly smaller than the electric power used in a conventional implanted cardioverter defibrillator provided with electrodes embedded inside of the heart. The larger electric power is, however, generally used for defibrillation, compared with cardiac pacing. Accordingly, in the case of setting the shapes and the positions of the defibrillation electrodes 102 and 108, it is preferable to set the widths of the defibrillation electrodes such as to ensure sufficiently efficient defibrillation, by taking into account the electric power supplied to the defibrillation electrodes.

It is not necessary to strictly satisfy all the conditions 1 to 3 required for setting the defibrillation electrodes. For example, part or the entirety of the conditions 1 to 3 may be eased by taking into account the position of the spiral wave reentry (point C) and the like.

Figure 3:
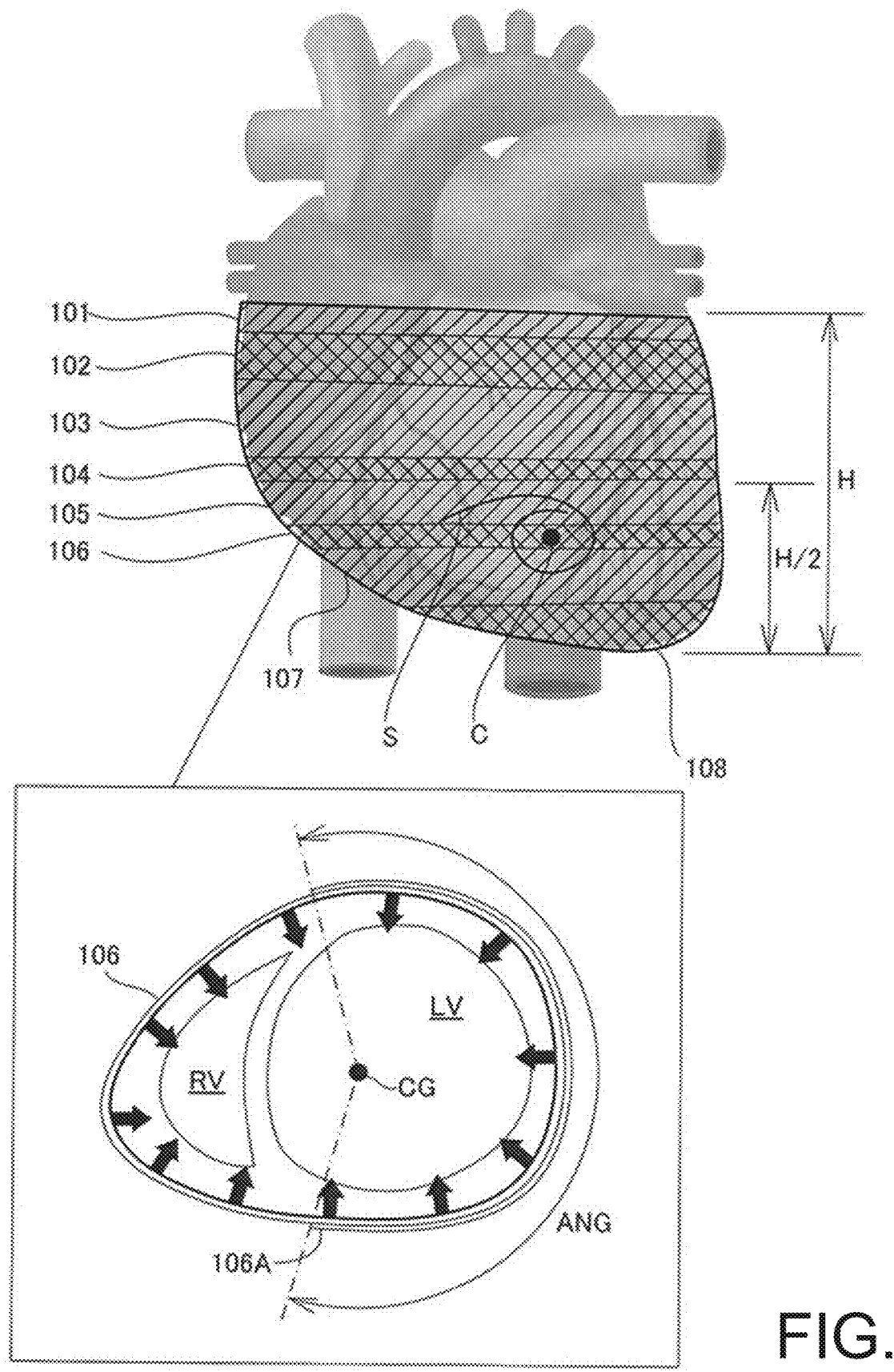
FIG. 3 is an explanatory diagram illustrating an example of placement locations of electrodes.

After setting the positions and the shapes of the defibrillation electrodes 102 and 108, the performer subsequently sets the positions and the shapes of the electrodes for pacing or more specifically the pacing electrodes 104 and 106 (step S12). Conditions required for setting are shown in the flowchart. A condition 1 is to place the pacing electrodes to overlay the center position of the spiral wave reentry (point C). This condition ensures effective cardiac pacing A condition 2 is to arrange the pacing electrodes to have the central angle (as shown by ANG in FIG. 3) of not smaller than 180 degrees. This condition further enhances the effect of cardiac pacing. It is not necessary to strictly satisfy the conditions 1 and 2 required for setting the pacing electrodes 104 and 106. For example, part or the entirety of the conditions 1 and 2 may be eased by taking into account the positions of the defibrillation electrodes and the like.

According to a modification, the cardiac net may be provided with only one pacing electrode 106 or may be provided with three or more pacing electrodes.

The order of execution of steps S10 to S12 may be changed. According to the embodiment, setting the defibrillation electrodes 102 and 108 (step S11) is performed prior to setting the pacing electrodes 104 and 106 (step S12). This is because the defibrillation electrodes 102 and 108 are thought to be of the higher importance as described previously.

After setting the defibrillation electrodes and the pacing electrodes, the performer performs overall weaving (step S13). When the shapes and the positions of the defibrillation electrodes 102 and 108 and the pacing electrodes 104 and 106 are determined, the shapes of the non-conductive portions 101, 103 and 107 are naturally determined to connect the defibrillation electrodes 102 and 108 and the pacing electrodes 104 and 106 with one another. The method employed for the overall weaving may be either a) a method of appropriately changing over the conductive thread and the non-conductive thread in the course of weaving the cardiac net having at least one electrode, so as to form the non-conductive portions, the defibrillation electrodes and the pacing electrodes; or b) a method of individually weaving the non-conductive portions, the defibrillation electrodes and the pacing electrodes and connecting the respective woven portions with one another.

The performer lastly weaves conductive wires into the respective electrodes (step S14). Illustration of the conductive wires is omitted. A leading end of each of the conductive wires may be connected with the connector 120 shown in FIG. 1 or may be directly connected with the lead 130. The cardiac net having at least one electrode is manufactured by the series of processes described above. The implanted cardioverter defibrillation device is configured as a whole by connecting the cardiac net having at least one electrode with the implanted cardioverter defibrillator body 200 by means of the lead 130.

The cardiac net having at least one electrode of the embodiment and the implanted cardioverter defibrillation device using this cardiac net having at least one electrode described above have various advantageous effects given below.

According to the embodiment, the pacing electrode 106 is provided to cover half the circumference or more of the cardiac ventricle. This configuration ensures effective pacing as described above with reference to FIG. 3.

Furthermore, according to the embodiment, the respective electrodes and non-conductive portions are configured by stretchable meshes. This configuration enables the electrodes to be placed along the heart and provides good electrical contact with the heart because of the stretchability. As a result, this configuration enables the functions of the respective portions to be performed effectively.

The present disclosure is not limited to the embodiment described above but may be implemented by a variety of other aspects within the scope of the present disclosure.

The present disclosure is applicable to implemented cardioverter defibrillators.

What is claimed is:

1. A cardiac net configured to be mounted on a heart to wrap outside of the heart, the cardiac net comprising:
   a non-conductive portion formed of a stretchable mesh made of a non-conductive thread;
   at least one defibrillation electrode formed of a stretchable mesh made of a conductive thread, the at least one defibrillation electrode being configured to be connected with a main device of an implantable cardioverter defibrillator or a cardiac resynchronization therapy defibrillator; and
   at least one pacing electrode configured for ventricular pacing and having an impedance higher than that of the at least one defibrillation electrode, the at least one pacing electrode being formed of a stretchable mesh made of a conductive thread and formed into a strip-like shape configured to be arranged on a lower side of and no higher than half a height of a cardiac ventricle to cover half a circumference or more of the cardiac ventricle substantially horizontally,
   wherein the at least one defibrillation electrode and the at least one pacing electrode are connected to the non-conductive portion so as to integrally form the cardiac net.

2. The cardiac net according to claim 1,
   wherein the at least one pacing electrode is configured to be arranged to cover an entire circumference of the cardiac ventricle.

3. The cardiac net according to claim 1,
   wherein the pacing electrode comprises a first pacing electrode and a second pacing electrode configured to be connected in parallel with the main device, the first and second pacing electrodes being formed into strips extending substantially parallel to each other configured to cover half a circumference or more of the cardiac ventricle substantially horizontally.

4. The cardiac net according to claim 1,
   wherein the pacing electrode is configured to be arranged to overlay a center of a spiral wave reentry that triggers ventricular fibrillation.

5. The cardiac net according to claim 1,
   wherein the at least one defibrillation electrode includes upper and lower defibrillation electrodes configured to be placed on an upper side and on a lower side of the heart, respectively, and
   wherein the at least one pacing electrode is provided between the upper and lower defibrillation electrodes.

6. The cardiac net according to claim 1,
   wherein the defibrillation electrode has an area larger than an area of the pacing electrode.

7. The cardiac net according to claim 1,
   wherein the non-conductive portion is made of an absorbable thread.

8. The cardiac net according to claim 1, further comprising:
   a connector having a jack mounted thereon,
   wherein the jack is configured to receive insertion of a lead that is standardized to connect with the main device, and
   the jack is connected with a conductive wire from each of the defibrillation electrode and the pacing electrode.

9. The cardiac net according to claim 8,
   wherein the conductive wire forms loops and is woven into the mesh that forms each electrode.

10. An implantable cardioverter defibrillation device, comprising:
    the cardiac net according to claim 1; and
    a main device that comprises either an implantable cardioverter defibrillator or a cardiac resynchronization therapy defibrillator,
    wherein the cardiac net and the main device are connected with each other by a conductive wire.

* * * * *